United States Patent
Lux et al.

(10) Patent No.: US 6,191,122 B1
(45) Date of Patent: *Feb. 20, 2001

(54) PARTIALLY HYDROPHOBIC PRECIPITATED SILICAS

(75) Inventors: Heinz-Günter Lux, Grosskrotzenburg; Karl Meier, Alfter; Astrid Müller, Gelnhausen; Rolf Oelmüller, Hanau; Anja Ramb, Rodenbach, all of (DE)

(73) Assignee: Degussa Hüls Aktiengesellschaft, Frankfurt am Main (DE)

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 08/829,542

(22) Filed: Mar. 28, 1997

Related U.S. Application Data (60) Provisional application No. 60/021,601, filed on Jul. 11, 1996.

(30) Foreign Application Priority Data

Mar. 29, 1996  (DE) ............................... 196 12 501

(51) Int. Cl.[7] ...................... C01B 33/12; C01B 33/18; A01N 57/12
(52) U.S. Cl. ................ 514/122; 423/335; 423/339; 424/489; 514/63
(58) Field of Search ................... 423/335, 339; 514/63, 122; 424/489

(56) References Cited

U.S. PATENT DOCUMENTS

| | | | |
|---|---|---|---|
| 3,830,738 | 8/1974 | Cottrell | 252/4 |
| 3,963,627 | * 6/1976 | Cottrell | 252/4 |
| 4,006,229 | * 2/1977 | Drabek | 424/225 |
| 4,273,589 | * 6/1981 | Nauroth et al. | 106/308 Q |
| 4,341,552 | 7/1982 | de Lange | 71/105 |
| 4,377,493 | * 3/1983 | Boylan et al. | 252/321 |
| 4,640,882 | * 2/1987 | Mitsuhashi et al. | 430/110 |
| 5,686,054 | * 11/1997 | Barthel et al. | 423/335 |

FOREIGN PATENT DOCUMENTS

| | | |
|---|---|---|
| 2149821 | 12/1995 | (CA) . |
| 1619865 | 3/1971 | (DE) . |
| 2 107 082 | 8/1971 | (DE) . |
| 2628975 C2 | 12/1977 | (DE) . |
| 2628975C2 | 12/1977 | (DE) . |
| 29 28 585A1 | 2/1980 | (DE) . |
| 2928585A1 | 2/1980 | (DE) . |
| 2107082 | 8/1991 | (DE) . |
| 4419234A1 | 12/1995 | (DE) . |
| 0 111 112A1 | 6/1984 | (EP) . |
| 0111112A1 | 6/1984 | (EP) . |
| 2630722 | 11/1989 | (FR) . |
| 1348372 | 3/1974 | (GB) . |
| 53369/93 | 3/1993 | (JP) . |
| 176462/96 | 7/1996 | (JP) . |

OTHER PUBLICATIONS

Derwent WPI, JP 5053369 A, Mar. 5, 1993.
Derwent WPI, JP 817462 A, Jul. 9, 1996.

* cited by examiner

Primary Examiner—Peter O'Sullivan
(74) Attorney, Agent, or Firm—Smith Gambrell & Russell, LLP (57) ABSTRACT

A partially hydrophobic precipitated silica having a methanol wettability of 10 to 49%, in particular with a DBP uptake on a dry basis of greater than 250 g/100 g and a mean particle size of 1 to 12 μm and/or a carbon content of 0.3 to 1.85% and/or a loss on drying of 2.6 to 10.0% and/or a pH value of 5.5 to 10.0, is prepared by mixing the amount of water-repellent agent with the precipitated silica suspension at very short residence time and low pH value, filtering off the solid substance, washing free of salt, drying, post-treating thermally and milling. The partially hydrophobic precipitated silica can be used in active substance formulations and active substance formulations of hydrolysis-sensitive substance and in defoaming agents.

19 Claims, 8 Drawing Sheets

PARTIALLY HYDROPHOBIC PRECIPITATED SILICAS

The present application claims priority under 35 U.S.C. §119 (e) (1) of U.S. provisional patent application having Ser. No. 60/021,601 filed Jul. 11, 1996 which is incorporated by reference in its entirety.

INTRODUCTION AND BACKGROUND

The invention relates to partially hydrophobic silicas, a process for their preparation, their use as carrier for hydrolysis-sensitive active substances and their use in defoaming agents.

The use of hydrophobic silicas in a hydrophobic liquid for the preparation of a defoaming agent is known (DE-C 2829906); U.S. Pat. No. 4,377,493; DE-C 3411 759; U.S. Pat. No. 4,344,858; Kalman Koczo et al., Journal of Colloid and Interface Science 166, 225–238 (1994), WO 95/05880).

Known defoaming agents consist of a mixture of non-polar oils and hydrophobic particles. The solids content is typically 1–20%. These mixtures are more effective defoaming agents than the oil or the hydrophobic particles alone. Defoaming agents are used in the textile, paper, paint, coating and detergent industries.

Known crop protection agents are substantially used in the form of wettable powders, as dust concentrates, dispersible granulates or as emulsifiable concentrates.

Known wettable powders (WP) consist of the following components:

Pesticide active substance, carrier, dispersing and wetting agents as well as optionally additional additives. Thorough premixing of these constituents is followed by coarse milling succeeded by fine milling. Use is in the form of an aqueous spray.

Known dust concentrates consist solely of active substance and filler. Formulations by analogy with the formulation of wettable powders. Fine milling is, however, often omitted.

The dust is applied as dust (DP) after blending with mineral fillers such as kaolin, talcum or dolomite.

Known dispersible granulates (WG) are solid formulations consisting of pesticide active substance, carrier, dispersing and wetting agent as well as optionally other additives. This mixture is finely milled and then granulated using known methods. Use takes the form of aqueous sprays.

Known emulsifiable concentrates (EC) are liquid and contain solvent-containing constituents. Attempts are made to replace the emulsifiable concentrates by solid formulations to avoid solvents that can pose a burden to the environment.

The use of hydrophilic precipitated silica as carrier in the preparation of crop protection agents, pest control agents or concentrated cattle feedstuffs is known (DE-B 16 19 865). The silicas conventionally used have a high oil uptake and a high absorption capacity.

The reduced storage stability of the active substances is, however, a disadvantage in the use of the known precipitated hydrophilic silicas in the preparation of agents containing active substances that are sensitive to hydrolysis. This applies in particular to active substances used in crop protection which could hitherto only be further processed as emulsifiable concentrates because of their sensitivity to hydrolysis.

Known hydrophobic precipitated silicas, such as the precipitated silicas according to DE 26 28975 C2, DE-C 27 29 244, DE-A 24 35 860, EP-A 492 124, and DE-A 25 13 608, are fully hydrophobized and therefore have the disadvantage of needing a large amount of wetting agent in the formulation.

It is therefore an object to provide a carrier for, in particular, hydrolysis-sensitive active substances, such as crop protection agents or feedstuffs as well as active substances from the chemical industry which ensures a longer storage stability of the active substance.

When defoaming agents are used, the known silica has the disadvantage that this silica sediments out when the defoaming agent is stored for longer periods, in particular with the use of low-viscous oils and a low solids content. The defoaming activity deteriorates because of sedimentation of the known silica. Moreover, the sedimented silica also has to be stirred up again in a laborious process before the defoaming agent is used. To prevent a tendency to sedimentation, it may be necessary to add a dispersing agent to the defoaming mixture, such as for example a pyrogenic silica, as well as the known silica (Degussa Technical Bulletin Pigments No. 42, page 11). This necessitates a change in the defoaming formulation which, in turn, necessitates further testing, makes the product more expensive and means an additional process step to work in the dispersing agent.

It is, for example, known from DE 28 29 906 C3 that the defoaming active substances may be prepared in such a manner as to achieve a high dispersion stability by adding to a mixture of a defoaming oil and an emulsifier first the hydrophobic and then the requisite amount of hydrophilic silica, with further stirring.

The instant invention has an advantage over this preparation in that the silica can be stirred into a defoaming oil in one process step and then dispersed, thereby obtaining a stable defoaming dispersion without an additional process step.

SUMMARY OF THE INVENTION

This invention relates to partially hydrophobic silicas, a process for their preparation, their use as a carrier for hydrolysis-sensitive active substances, and their use in defoaming agents.

Partially hydrophobic precipitated silicas according to the invention have a methanol wettability of 10–49%. The partially hydrophobic precipitated silicas can comprise 85–98% by weight of precipitated silica and 2–15% by weight of a water-repellent agent.

A process for the preparation of partially hydrophobic silicas comprises mixing a water-repellent agent with a precipitated silica suspension using high shearing forces, filtering the water-repellent agent-containing precipitated silica suspension to form a filter cake, wherein the water-repellent agent-containing precipitated silica suspension is mixed in a predetermined ratio, at a low pH, and for a very short residence time, washing the filter cake to remove salt and forming a filter cake having a homogenous mixture of precipitated silica and water-repellent agent, drying the homogeneous filter cake, thermally post-treating or tempering the dried filter cake, and milling the dried, treated filter cake to form the partially hydrophobic precipitated silica, wherein the partially hydrophobic precipitated silica has a methanol wettability of 10–49%.

Partially hydrophobic silicas can be used as carriers for hydrolysis-sensitive active substances and in defoaming agents.

DETAILED DESCRIPTION OF THE INVENTION

One object of the invention is achieved with a partially hydrophobic precipitated silica which has a methanol wettability in a range between any two real numbers from 10 to 49%. The precipitated silica of the invention may have a DBP-uptake (dried substance) of greater than 250 g/100 g (DBP number) and optionally a mean particle size of in a range between any two real numbers from 1–12 μm.

The partially hydrophobic precipitated silica of the invention can have a carbon content in a range between two real numbers from 0.3 to 1.85%, preferably 0.5 to 1.5% and/or a pH value in the range between two real numbers from 5.5 to 10 and/or a loss on drying in the range between two real numbers from 2.6 to 10%, preferably 3 to 6%.

In particular, the partially hydrophobic precipitated silica of the invention can have one or several of the following physical chemical characteristic values:

| | |
|---|---|
| Surface (BET), m²/g | 75–250 |
| Tamped density, g/l (DIN ISO 787/11) | 70–150 |
| Loss on drying 2h/105° C., % (DIN ISO 787/2) | 2.6–10.0 |
| Loss at red heat related to 2h/105° C. dried substance, % (DIN ISO 3262/11) | 2.5–7.5 |
| pH value, 5% (methanol-aqueous soln.) (DIN ISO 787/9) | 5.5–10 |
| Conductivity (methanol-aqueous soln.) | ≦600 (μS/cm) |
| DBP uptake, dried substance, g/100 g | ≧250 |
| Methanol wettability, titrated, % | 10–49 |
| Mean particle size, Coulter counter μm | 1–12 |
| Carbon content, % | 0.3–1.85 |
| SiO$_2$, % (DIN ISO 3262/19) | ≧98 |

The above values include all real numbers in the specified range.

The silica may be a precipitated silica which has been treated with a water-repellent agent after its production and/or also during its production in order to obtain the above-described characteristics.

Precipitated silicas are known from Ullmanns Enzyklopädie der technischen Chemie, 4th edition, volume 21, pages 458 to 473 (1988).

The production of fully hydrophobic silicas is, for example, known from DE 44 19 234 A1, DE-C 27 29 244, DE 26 28 975 C2 and DE-OS 21 07 082. DE 26 28 975 C2 and DE-C 27 29 244 relate to fully hydrophobic precipitated silicas. The two other patent specifications or unexamined German publications relate to fully hydrophobic and partially hydrophobic, pyrogenic silicas with different physical chemical characteristics that are not identical with the characteristics of the precipitated silica of the invention.

The use of fully hydrophobic pyrogenic silicas for dusting onto pesticide granulates is described in DE 29 28 585 A1, the use of pyrogenic silicas as additive in active substance formulations is explained in EP 0 111 112 A1.

The partially hydrophobic precipitated silica of the invention can comprise from 85 to 98% by weight of precipitated silica and 15 to 2% by weight of water-repellent agent (silicone oil that can have a carbon content of 32.4%). To obtain the desired degree of water-repellence, it can be prepared by mixing the requisite amount of water-repellent agent using high shearing forces with precipitated silica suspension prepared using a known process according to a given ratio with very short residence time and low pH value, filtering off the water-repellent agent-containing precipitated silica suspension and washing this free of salt, drying the precipitated silica filter cake homogeneously mixed with water-repellent agent using a known process, providing thermal post-treatment or tempering and then carrying out mechanical or radiation milling.

It is, in particular, possible to mix silicone oil homogeneously using high shearing energy with precipitated silica suspension produced using known processes, with or without addition of phase transmitters (e.g. wetting agents, emulsifiers). The continuous shearing device that may be used may be an Ultra-Turrax, a Kothoff-Mischsirene or a Rheinhütte mixer. The precipitated silica suspension homogeneously mixed with water-repellent agent is then separated using known filtration apparatuses (e.g. chamber filtration press, rotary filter) and the solid matter containing water-repellent agent is washed free of salt. In so doing, the water-repellent agent is entirely taken up by the precipitated silica filter cake. The filtrates yielded are no longer contaminated with organosilicon compounds, with the result that the measured TOC contents are <10 mg/l.

The precipitated silica suspensions used in the mixing process and the water-repellent agent are characterized by the following physical chemical material data:

Precipitated silica A (the substance data relate to a filtered, washed and dried precipitated silica sample, without added water-repellent agent):

| | |
|---|---|
| BET surface according to DIN 6613 | 150 ± 50 [m$^2$/g] |
| Mean size of primary particles from EM photos | 15–25 [nm] |
| Loss on drying according to DIN 55921 after 2 h at 105° C. | 2.5–4.5 [%] |
| Loss at red heat (related to the substance dried for 2 h at 105° C. according to DIN 55921) | 3 ± 0.5 [%] |
| pH value (in 5% aqueous dispersion according to DIN 53200) | 3.5–6.5 |
| Conductivity (in 4% aqueous dispersion) | <1000 [µS] |
| SO$_3$ content (related to the substance dried for 2h at 105° C. according to DIN 55921) | 0.3 [%] |
| Na$_2$ content (related to the substance for dried 2h at 105° C. according to DIN 55921) | 0.3 [%] |

The above values includes all real numbers within the specified range.

Precipitated silica B (the substance data relate to a filtered, washed and dried precipitated silica, without added water-repellent agent):

| | |
|---|---|
| BET surface according to DIN 66131 | 300 ± 50 [m$^2$/g] |
| Mean size of primary particles from EM photos | 10–15 [nm] |
| Loss on drying according to DIN 55921 after 2 h at 105° C. | 2.5–4.5 [%] |
| Loss at red heat (related to the substance dried for 2h at 105° C. according to DIN 55921) | 3 ± 0.5 [%] |
| pH value (in 5% aqueous dispersion according to DIN 53200) | 3.5–6.5 |
| Conductivity (in 4% aqueous dispersion) | <1000 [µS] |
| SO$_3$ content (related to the substance dried for 2h at 105° C. according to DIN 55921) | <0.3 [%] |
| Na$_2$O content (related to the substance dried for 2h at 105° C. according to DIN 55921) | <0.3 [%] |

The above values include all real numbers in the specified range.

For hydrophobizing it is, in particular, possible to use silicone oil, comprising dimethylpolysiloxanes with a viscosity of 20 to 1000 mpas, preferably with 50 mPas as water-repellent agents. It is also possible to use: $R_2R'Si$, where $R=CH_3O-$, $C_2H_5O-$, $Cl-$, $R'=CH_3-$, $C_2H_5-$, HMDS (hexamethyl disilazane), D4 (octamethyl tetrasiloxane), D6, D8, $R_3Si-C_nH_{2n+1}$, where n=1–18, $R=CH_3O-$, $C_2H_5O-$, $C_3H_7O-$, $Cl-$, in particular Si 108 (trimethoxyoctyl silane), Si 116, polymethyl siloxanes, polymethyl siloxane emulsions, (trimethyloxyhexadecyl silane), aminopropyl silanes, vinyl silanes, methacrylic silanes.

The resultant precipitated silica filter cake homogeneously mixed with water-repellent agent is dried in the subsequent process step in known drying aggregates. The drying aggregate for drying the water-repellent agent-containing filter cake can be a band dryer or spin-flash dryer. To achieve the desired degree of water-repellence, the dry product containing water-repellent agent is subjected to thermal post-treatment at 300° C. to 400° C., preferably 350° C. for 30 to 60 minutes in a discontinuous, electrically heated stirrer container or in a continuous electrically heated double screw reactor thermally treated or tempered and then milled mechanically or using jet mills.

Compared with the above-described preparation comparable in principle with known processes, the partially hydrophobic precipitated silica of the invention can in particular be prepared according to the following process of wet water-repellence which cannot be deduced from the state of the art.

A mass stream of 0.424 kg/h polymethyl siloxane is added using a continuous mixer with high shearing energy input to a mass stream of 160 kg/h of an aqueous precipitated silica suspension with a solids content of 85 g/l, that was prepared using known manufacturing processes, while maintaining a pH value of 3, the temperature of the two components to be mixed being 25±5° C. In so doing, the residence time in the mixer may not exceed 5 seconds. The command reference input for the coating process is taken to be the dimensionless coating index $B_i$ which describes the ratio to one another of the active substance portions of the two mass streams to be mixed. A coating index of 32 is needed to achieve the hydrophobic property of the precipitated silica of the invention.

The precipitated silica coated with silicone oil is then separated using known processes without using a subsequent post-reaction time, washed almost free of electrolyte, dried at 105° C., tempered for 1.0 hour at 370° C. and then milled.

It has been found that the silica of the invention can be prepared in the mixer due in particular to the low pH value and the short residence time in the mixer.

A. Methanol Wettability

Methanol wettability, which is a measure of the water-repellence, is determined as follows:

1. Basic Principles

Silicas, the surfaces of which are modified with non-hydrolyzable organic groups, are generally not wetted with water. These hydrophobic silicas can, however, be wetted using a methanol/water mixture. The proportion of methanol in this mixture, expressed in percent by weight, is a measure of the water-repellence of the modified silica. The higher the proportion of methanol, the better the substance is hydrophobized.

2. Apparatus and Reagents

A 20 ml measuring pipette with graduation of scale A 250 ml separating funnel Methanol p.a.

3. Method 200 mg of the hydrophobic silica and 50 ml water are added to a 250 ml separating funnel. The silica remains on the surface of the water. The tip of the measuring pipette filled with methanol is then immersed in the liquid phase (to prevent direct contact between the silica and the pure methanol) and the methanol is allowed to run in slowly. In so doing, the separating funnel is shaken with a circular movement of the hand so that a vortex arises in the liquid. Methanol is added until the solid substance is wetted. This is the case when     a) the silica is no longer distributed over the entire surface of the liquid phase (already containing methanol) and the relatively clear, film-free liquid becomes visible.

b) the silica film forming over the phase limiting surface at the wall of the separating funnel disappears.

c) moist silica agglomerates remain adhering to the wall of the separating filter on shaking.

4. Calculation

Methanol wettability is given in % by weight methanol of the methanol/water mixture according to the formula:

$$\text{Methanol wettability} = \frac{0.79x \cdot 100}{0.79 + 50}$$

x=methanol consumption in ml

In this method, methanol consumption can differ by 2 ml with the same person and the same sample.

B. DBP Uptake

DBP uptake (DBP-number), which is a measure of the absorbency of the precipitated silica, is determined as follows:

1. Basic Principles

The dibutylphthalate number is determined using a Brabender plastograph. The DBP number is a measure of the liquid absorbency or absorption capacity of a product in powder form. Absorption capacity depends on moisture content, on granulation and initial weight of the material investigated.

2. Apparatus and Reagents

Brabender plastograph with plotter
Multi-Dosimat E 415 (50 l) manufactured by Metrohm
Dibutylphthalate 3. Method 12.5 g silica are added to the kneader of the Brabender plastograph. Dibutylphthalate flows into the mixture at a speed of 4 ml/minute with constant mixing (revolution speed of the kneader paddles 125 rpm) Power consumption is low during mixing. Towards the end of the determination the mixture becomes poorly flowing. This fact is documented by a rise in power consumption which is shown on a scale. Addition of DBP is automatically discontinued at a scale reading of 300.

4. Calculation

The density of DBP is 1.047 g/ml.

$$\% \text{ by weight DBP uptake} = \frac{\text{ml DBP} \cdot 1.047 \cdot 100}{12.5}$$

The DBP uptake is related to the anhydrous, dried substance. When using precipitated silicas with higher moisture contents, the value must be corrected using the correction table if these precipitated silicas are not dried before determining the DBP number. Use of the correction table can lead to clear deviations compared to a determination of dried precipitated silicas.

Correction table for dibutylphthalate uptake anhydrous (Add correction values corresponding to the water content to the value obtained)

| % Water→ | % Dibutylphthalate | | | | |
|---|---|---|---|---|---|
| ↓ | .0 | .2 | .4 | .6 | .8 |
| 0 | 0 | 2 | 4 | 5 | 7 |
| 1 | 9 | 10 | 12 | 13 | 15 |
| 2 | 16 | 18 | 19 | 20 | 22 |
| 3 | 23 | 24 | 26 | 27 | 28 |
| 4 | 28 | 29 | 29 | 30 | 31 |
| 5 | 31 | 32 | 32 | 33 | 33 |
| 6 | 34 | 34 | 35 | 35 | 36 |
| 7 | 36 | 37 | 38 | 38 | 39 |
| 8 | 39 | 40 | 40 | 41 | 41 |
| 9 | 42 | 43 | 43 | 44 | 44 |
| 10 | 45 | 45 | 46 | 46 | 47 |

| | DBP uptake Initial weight 12.5 g  F = 8.376 | | | | | | | | | |
|---|---|---|---|---|---|---|---|---|---|---|
| ml DBP consumption→ | % DBP uptake | | | | | | | | | |
| ↓ | .0 | .1 | .2 | .3 | .4 | .5 | .6 | .7 | .8 | .9 |
| 15 | 126 | 126 | 127 | 128 | 129 | 130 | 131 | 132 | 132 | 133 |
| 16 | 134 | 135 | 136 | 137 | 137 | 138 | 139 | 140 | 141 | 142 |
| 17 | 142 | 143 | 144 | 145 | 146 | 147 | 147 | 148 | 149 | 150 |
| 18 | 151 | 152 | 152 | 153 | 154 | 155 | 156 | 157 | 157 | 158 |
| 19 | 159 | 160 | 161 | 162 | 162 | 163 | 164 | 165 | 166 | 167 |
| 20 | 168 | 168 | 169 | 170 | 171 | 172 | 173 | 173 | 174 | 175 |
| 21 | 176 | 177 | 178 | 178 | 179 | 180 | 181 | 182 | 183 | 183 |
| 22 | 184 | 185 | 186 | 187 | 188 | 188 | 189 | 190 | 191 | 192 |
| 23 | 193 | 193 | 194 | 195 | 196 | 197 | 198 | 199 | 199 | 200 |
| 24 | 201 | 202 | 203 | 204 | 204 | 205 | 206 | 207 | 208 | 209 |
| 25 | 209 | 210 | 211 | 212 | 213 | 214 | 214 | 215 | 216 | 217 |
| 26 | 218 | 219 | 219 | 220 | 221 | 222 | 223 | 224 | 224 | 225 |
| 27 | 226 | 227 | 228 | 229 | 230 | 230 | 231 | 232 | 233 | 234 |
| 28 | 235 | 235 | 236 | 237 | 238 | 239 | 240 | 240 | 241 | 242 |
| 29 | 243 | 244 | 245 | 245 | 246 | 247 | 248 | 249 | 250 | 250 |
| 30 | 251 | 252 | 253 | 254 | 255 | 255 | 256 | 257 | 258 | 259 |
| 31 | 260 | 260 | 261 | 262 | 263 | 264 | 265 | 266 | 266 | 267 |
| 32 | 268 | 269 | 270 | 271 | 271 | 272 | 273 | 274 | 275 | 276 |
| 33 | 276 | 277 | 278 | 279 | 280 | 281 | 281 | 282 | 283 | 284 |
| 34 | 285 | 286 | 286 | 287 | 288 | 289 | 290 | 291 | 291 | 292 |
| 35 | 293 | 294 | 295 | 296 | 297 | 297 | 298 | 299 | 300 | 301 |
| 36 | 302 | 302 | 303 | 304 | 305 | 306 | 307 | 307 | 308 | 309 |
| 37 | 310 | 311 | 312 | 312 | 313 | 314 | 315 | 316 | 317 | 317 |
| 38 | 318 | 319 | 320 | 321 | 322 | 322 | 323 | 324 | 325 | 326 |
| 39 | 327 | 327 | 328 | 329 | 330 | 331 | 332 | 333 | 333 | 334 |
| 40 | 335 | 336 | 337 | 338 | 338 | 339 | 340 | 341 | 342 | 343 |
| 41 | 343 | 344 | 345 | 346 | 347 | 348 | 348 | 349 | 350 | 351 |
| 42 | 352 | 353 | 353 | 354 | 355 | 356 | 357 | 358 | 358 | 359 |

-continued

DBP uptake
Initial weight 12.5 g  F = 8.376

| ml DBP consumption→ | % DBP uptake | | | | | | | | | |
|---|---|---|---|---|---|---|---|---|---|---|
| ↓ | .0 | .1 | .2 | .3 | .4 | .5 | .6 | .7 | .8 | .9 |
| 43 | 360 | 361 | 362 | 363 | 364 | 364 | 365 | 366 | 367 | 368 |
| 44 | 369 | 369 | 370 | 371 | 372 | 373 | 374 | 374 | 375 | 376 |
| 45 | 377 | 378 | 379 | 379 | 380 | 381 | 382 | 383 | 384 | 384 |

Determining the particle size (Coulter counter)
Application: The determination of particle size (characteristic particle size curve) of silicas using the Coulter counter occurs in an agueous electrolyte solution (isotone II).

Determination Method

The beakers (2 per count), the magnet and the pipette tips are blown dust-free in a stream of nitrogen at 5–6 bar. The beakers are then inverted on dust-free lens paper, the magnet and the pipette tips being placed into a petri dish that has also been blown out.

0.100 g of the substance to be examined are weighed on an analytical balance and transferred to the beaker. The magnet is added, first moistened with a little isotonic solution and then filled up to the 60 ml mark with isotone. The suspension is then stirred with the magnetic stirrer for ½ minute at setting 3 (scale 1–10). The beaker is then suspended in the ultrasonic bath and sonicated for exactly 1 minute. In so doing, care must be taken to ensure that the depth of immersion in the distilled water of the ultrasonic bath reaches exactly to the 60 ml marking of the beaker. After sonication, the beaker is replaced on the magnetic stirrer and a sample of the suspension is removed using the automatic pipette during stirring (setting 3 again). The total amount removed should be used for the count. If a little less suspension is needed, less suspension should be drawn into the tip of the pipette.

The second 100 ml beaker is filled with isotone II solution, placed on the beaker platform and the capillary (100 μm) and the stirrer immersed. The stirrer is set to a moderate speed.

Solutions and Apparatus 100 ml beakers
Automatic pipette—Pipetman manufactured by Gilson
Plastic pipette tips
Magnetic stirrer and magnet (length 3 mm)
Ultrasonic bath: Bandelin, Sonorex RK 102
Analytical balance
Dust-free lens paper
Nitrogen bottle with drying device and nozzle
Petri dish
Stopwatch
Grain analysis paper
Isotone II solution
Coulter counter model TA II The silica of the invention can be used to manufacture crop protection agents with active substances sensitive to hydrolysis. In so doing it is possible to manufacture wettable powders or water-dispersible granulates which can be used in water soluble foil bags in outer cardboard packagings. This achieves advantages during transport, with hazardous substance classification, with savings in wasted packaging and the cost reductions associated therewith.

The silica of the invention can, in particular, be used when making use of active substances of the group of phosphoric acid esters (malathion, diazinone, etc.).

The form of application of every other active substance may be formulated by analogy.

The active substance formulations prepared using the silica of the invention, such as for example crop protection agents have the additional advantage of long active substance storage stability.

EXAMPLES

Example 1

Storage of 50 WP Malathion and Active Substance Stability

Preparation as 50 WP Malathion

A premix is first prepared in the ratio 1:1 using Wessalon S and the wetting agent Ampholak XIO. 28 g of the partially hydrophobic precipitated silicas as well as Wessalon S as comparison substance are briefly fluidized in a 500 ml Quickfit stirring apparatus. 52.1 g malathion (96%) are then gradually added dropwise before adding 6 g of the premix as well as 3.0 g Empikol LZ/P dispersing agent. 10.9 g filler (Rollokalk) are subsequently mixed therewith and the mixture is homogenized using a Turbula mixer.

The samples are stabilized by storing them for 4 days at room temperature. The initial values of CIPAC suspension and the malathion contents are then determined according to CIPAC. The initial values of malathion according to WHO and isomalathion according to WHO are also determined after 4 days and the samples then stored at 54° C. and measured after 7 days, 14 days, 28 days and 56 days.

Testing Suspension According to CIPAC-12/3/(M) 1 Before and After Storage at 54° C.

This method is a spectroanalytical process with UV as light source. Malathion reacts/hydrolyzes with alkali in Na-OO-dimethyldithiophosphate and is converted with Cu/Fe solution into a yellow copper complex and measured at 420 μm. The influence of wetting agent on malathion release is presumably great in the case of this method.

Testing Malathion Content According to WHO/SIF/ 10.R5 Using Gas Chromatography Before and After Storage at 54° C.

The method is based on separation of a substance mixture through substance-specific distribution between stationary phase (column) and a stream of carrier gas which lead to different speeds/retention times. In this method, there is an extraction equilibrium between solvent and silica during detachment of the malathion from the silica that may possibly favor the hydrophobic silica types. The wetting agent presumably exerts hardly any influence.

Testing Isomalathion Content After WHO/SIF/ 10.R5 Using HPLC Before and After Storage at 54° C.

To determine the isomalathion content, 0.6 g 50 WP malathion are weighed in and mixed with 65% aqueous acetonitrile solution for 30 minutes. The sample is measured against a reference solution after centrifugation and filtration. With this method there is also an extraction equilibrium between solvent and silica that may possibly favor the hydrophobic silica. The wetting agent presumably exerts hardly any influence.

Example 2

Storage of 1:1 Malathion Concentrates and Active Substance Stability

The active substance solution (96%) is applied to the partially hydrophobic carrier in a ratio of 1:1. This mixture is then tested for storage stability. The values obtained in this manner are exclusively attributable to the effect of the carrier.

The tests employed in the examples section are described as:

Malathion 1:1 Formulation 28 g malathion (96%) are added dropwise within 30 minutes to 28 g carrier and then post-stirred for 3 minutes and mixed at a medium setting in a Turbula mixer for 5 minutes.

It is striking that the mixtures are markedly drier compared to the previously formulated 50 WP malathion (28 g hydrophobic carrier+52.1 g malathion+residual formulation constituents).

Testing Malathion Content According to CIPAC 12/ 3 (MI) 1 by Means of UV/VIS Before and After Storage at 54° C.

Storage by analogy with 50 WP malathion.

Testing Malathion Content According to WHO/SIF/ 10.R5 by Means of GC Before and After Storage at 54° C.

Storage by analogy with 50 WP malathion.

TABLE 1

| Precipitated silica | Methanol wettability titrated % | pH | Surface m²/g | DBP uptake, original material g/100g | DBP uptake, anhydrous g/100g | Carbon % | Mean particle size Coulter Counter μm |
|---|---|---|---|---|---|---|---|
| Standard (Wessalon S) | — | 6.3 | 182 | 240 | 272 | 0.05 | 8.2 |
| Silica No. 1 (comparison) | 43 | 7.5 | 121 | 291 | 297 | 2.4 | 7.7 |
| Silica No. 2 (comparison) | 48 | 7.8 | 189 | 260 | 282 | 2.3 | 5.3 |
| Silica No. 3 | 20 | 7.8 | 209 | 259 | 283 | 1.6 | 5.3 |
| Silica No. 4 | 28 | 7.3 | 94 | 233 | 250 | 1.0 | 11.8 |
| Standard (Sipernat D10) | 62 | 9.4 | 113 | n.c. | n.c. | 2.9 | 4.3 |
| Silica No. 5 | 49 | 6.9 | 150 | 226 | 257 | 0.5 | 7.4 |
| Silica No. 6 | 49 | 7.7 | 160 | 235 | 265 | 0.9 | 3.5 |

| Precipitated silica | Tamped density g/l | Loss on drying % | Loss at red heat % | Conductivity μS/cm | Sieve residue Mocker >45 μm % | SiO₂ % | Na₂O % | Fe₂O₃ ppm | Sulfate as SO₃ % |
|---|---|---|---|---|---|---|---|---|---|
| Standard (Wessalon S) | 107 | 5.3 | 4.4 | 710 | 0.06 | n.c. | n.c. | n.c. | n.c. |
| Silica No. 1 (comparison) | 152 | 0.7 | n.c. | n.c. | n.c. | n.c. | n.c. | n.c. | n.c. |
| Silica No. 2 (comparison) | 139 | 2.8 | n.c. | n.c. | n.c. | n.c. | n.c. | n.c. | n.c. |
| Silica No. 3 | 122 | 3.2 | 3.8 | 62 | 0.02 | 99.5 | 0.15 | 315 | 0.03 |
| Silica No. 4 | 125 | 4.9 | 2.8 | 124 | 0.02 | 99.1 | 0.20 | 347 | 0.08 |
| Standard (Sipernat D10) | 106 | 2.8 | 6.2 | 330 | n.c. | n.c. | n.c. | n.c. | n.c. |
| Silica No. 5 | 133 | 5.0 | 3.9 | 390 | 0.04 | 98.8 | 0.68 | 346 | 0.8 |
| Silica No. 6 | 96 | 4.7 | 4.3 | 380 | <0.01 | 98.8 | 0.93 | 334 | 0.95 | n.c. = not calculated

TABLE 2

Trial results (use as carrier)
Results of the technical application and active substance examination results of 50 WP malathion

| | | Standard (Wessalon S) | Precipitated silica No. 1* | Precipitated silica No. 2* | Precipitated silica No. 3 |
|---|---|---|---|---|---|
| After 4 days at RT | AT (C) in % | 94.2 ± 0.45 | 87.9 ± 0.46 | 91.0 ± 1.30 | 94.0 ± 0.80 |
| | ZFE (M2)in % | 54.3 | 50.5 | 52.7 | 49.8 |

TABLE 2-continued

Trial results (use as carrier)
Results of the technical application and active substance examination results of 50 WP malathion

|  |  | Standard (Wessalon S) | Precipitated silica No. 1* | Precipitated silica No. 2* | Precipitated silica No. 3 |
|---|---|---|---|---|---|
| (Initial w.) | (M)in % | 49.3 ± 0.65 | 50.0 | 48.8 |  |
|  | (I)in % | <0.025 ± 0 | <0.025 | <0.025 | <0.025 |
| After 7 days' storage at 54° C. | AT (C)in % | 85.9 ± 0.90 | 89.6 ± 1.51 | 88.3 ± 0.78 | 92.3 ± 0.56 |
|  | ZFE (M2)in % | 45.1 | 41.2 | 45.4 | 45.3 |
|  | (M)in % | 49.6 | 47.6 | 47.0 | 48.5 |
|  | (I)in % | 0.65 | 0.79 | 0.47 | 0.56 |
| After 14 days' storage at 54° C. | AT (C) in % | 86.4 ± 0.34 | 89.2 ± 3.11 | 87.4 ± 1.70 | 93.3 ± 0.46 |
|  | ZFE (M2)in % | 37.6 | 45.2 | 46.3 | 43.8 |
|  | (M)in % | 47.0 ± 0.53 | 48.8 | 45.1 | 46.5 |
|  | (I)in % | 0.97 ± 0.03 | 1.39 | 0.93 | 0.99 |
| After 28 days' storage at 54° C. | AT (C) in % | 87.4 ± 1.22 | 81.4 ± 0.78 | 81.9 ± 2.99 | 84.2 ± 2.35 |
|  | ZFE (M2)in % | 40.9 | 42.6 | 44.7 | 44.3 |
|  | (M)in % | 45.9 | 47.9 | 48.7 | 45.1 |
|  | (I)in % | 1.06 | 1.23 | 0.98 | 0.98 |
| After 56 days' storage at 54° C. | AT (C) in % | 90.2 ± 4.53 | 74.2 ± 3.20 | 75.8 ± 4.17 | 77.0 ± 2.25 |
|  | ZFE (M2)in % | 30.5 | 34.7 | 40.0 | 36.1 |
|  | (M)in % | 44.0 | 46.0 | 40.7 | 42.9 |
|  | (I)in % | 1.94 | 2.70 | 1.66 | 2.16 |

*Comparative example

TABLE 3

Deviations, absolute in % (initial value-measured value) after storage at 54° C. of the 50 WP malathion

|  |  | Standard (Wessalon S) | Precipitated silica No. 1* | Precipitated silica No. 2* | Precipitated silica No. 3 |
|---|---|---|---|---|---|
| Initial value after 4 days' at RT | AT (C) in % | 94.2 ± 0.45 | 87.9 ± 0.46 | 91.0 ± 1.30 | 94.0 ± 0.80 |
|  | ZFE (M2)in % | 54.3 | 50.5 | 52.7 | 49.8 |
|  | (M)in % | 49.3 ± 0.65 | 50.0 | 48.8 |  |
|  | (I)in % | <0.025 ± 0 | <0.025 | <0.025 | <0.025 |
| Deviation after 7 days' storage at 54° C. | AT (C)in % | -8.3 | ± 1.7 | -2.7 | -1.7 |
|  | ZFE (M2)in % | -9.2 | -9.3 | -7.2 | -4.5 |
|  | (M)in % | ± 0.3 | -2.4 | -1.8 | -0.5 |
|  | (I)in % | ± 0.625 | ± 0.765 | ± 0.445 | ± 0.535 |
| Deviation after 14 days at 54° C. | AT (C) in % | -7.8 | ± 1.3 | ± 2.3 | -5.3 |
|  | ZFE (M2)in % | -16.7 | -5.3 | -6.4 | -6.0 |
|  | (M)in % | -2.3 | -1.2 | -3.7 | -2.5 |
|  | (I)in % | ± 0.945 | ± 1.365 | ± 0.905 | ± 0.965 |
| Deviation after 28 days at 54° C. | AT (C) in % | -6.8 | -6.5 | -9.1 | -9.8 |
|  | ZFE (M2)in % | -13.4 | -7.9 | -8.0 | -5.5 |
|  | (M)in % | -3.4 | -2.1 | -3.1 | -3.9 |
|  | (I)in % | ± 1.035 | ± 1.205 | ± 0.955 | ± 0.955 |
| Deviation after 56 days at 54° C. | AT (C) in % | -4.0 | -13.7 | -15.5 | -17.0 |
|  | ZFE (M2)in % | -23.8 | 15.8 | -12.7 | -13.7 |
|  | (M)in % | -5.3 | -4.0 | -8.1 | -6.1 |
|  | (I)in % | ± 1.915 | ± 2.675 | ± 1.635 | ± 2.135 |

*Comparative example

TABLE 4

Active substance analytical examination results of the 1:1 malathion concentrates

|  | Standard (Wessalon S) | Precipitated silica No. 3 | Precipitated silica No. 1* | Precipitated silica No. 5 | Precipitated silica No.4 |
|---|---|---|---|---|---|
| Initial value 1 day RT | 48.4 1.33 | 49.2 0.27 | 52.3 2.39 | 46.8 1.28 | 48.9 ± 0.09 |
| ZFE (M, GC) in % | 44.8 | 55.4 | 47.1 | 46.1 | 50.7 |
| ZFE (M2, UV) in % |  |  |  |  |  |
| After 7 days 54° C. |  |  |  |  | 57.1 ± 0.7 |
| ZFE (M, GC) in % | 46.1 0.98 | 48.5 0.27 | 46.8 1.12 | 46.2 1.11 | 51.2 |

TABLE 4-continued

Active substance analytical examination results of the 1:1 malathion concentrates

|  | Standard (Wessalon S) | Precipitated silica No. 3 | Precipitated silica No. 1* | Precipitated silica No. 5 | Precipitated silica No.4 |
|---|---|---|---|---|---|
| ZFE (M2, UV) in % | 40.7 | 45.6 | 41.7 | 41.7 |  |
| After 14 days 54° C. | 55.1 |  |  |  |  |
| ZFE (M, GC) in % | 43.8 0.81 | 48.3 0.86 | 48.1 0.40 | 46.1 5.68 | 47.7 |
| ZFE (M2, UV) in % | 40.5 | 42.8 | 47.6 | 38.7 |  |
| After 29 days 54° C. |  |  |  |  | 51.3 ± 0.5 |
| ZFE (M, GC) in % | 40.6 2.44 | 46.7 0.26 | 46.9 1.25 | 43.5 0.34 | 38.9 |
| ZFE (M2, UV) in % | 36.1 | 45.4 | 41.1 | 35.2 |  |
| After 56 days 54° C. |  |  |  |  | — |
| ZFE (M, GC) in % | 34.3 1.60 | 44.9 0.45 | 44.3 0.32 | 39.7 1.17 | — |
| ZFE (M2, UV) in % | 34.5 | 41.9 | 43.9 | 33.3 |  |

ZFE (M1 GC) = Malathion content according to WHO using GC
*Comparative example
ZFE (M2, UV) = Malathion content according to CIPAC using UV/VIS
AT (C) = CIPAC suspension power
ZFE (M) = Malathion content according to WHO using GC
ZFE (M2) = Malathion content according to CIPAC using UV/VIS
(M) = Malathion content according to WHO using GC
(I) = Isomalathion content according to WHO using HPLC The possible influences of, for example, wetting agents on the accuracy of measurements should be considered when evaluating the results of the Fischer suspension power and of the malathion contents and the isomalathion contents of the 50 WP malathion.

The process error when determining the malathion content according to CIPAC using UV/VIS is given as 5% malathion. A double determination that shows a standard deviation of 0.7% is carried out on one sample after 14 days.

The malathion contents according to WHO show a standard deviation between 0.1 and 0.7%. The standard deviation of the isomalathion contents, with two double determinations in the total series of measurements, is 0 to 0.03%.

The results of the active substance stability are shown graphically in FIGS. 1 to 5.

The trials show that the active substance stability can be increased by using the partially hydrophobic precipitated silicas of the invention and that wetting and dispersing agents can be economized on, for example, in crop protection formulations in comparison to known fully hydrophobic precipitated silicas.

Example 3

Preparation of the Defoaming Dispersions

To prepare the 5% defoaming dispersions 57 g of the corresponding oil, for example Shell Risella G 118 (now Shell Risella G 18), viscosity 40 cSt., are prepared in 250 ml beakers, 3 g of the silica of the invention or of Sipernat D10 are then added and carefully stirred together. Dispersing then occurs using an Ultra Turrax T50 at 10000 rpm for 5 minutes.

Stability Testing of the Defoaming Dispersions

For this purpose the still hot dispersions are filled into 100 ml glass cylinders, stored in a vibration-free location at room temperature and any possible phase separation recorded at regular time intervals (value in ml clear oil phase).

| | Trial result (use in defoaming agent) | |
|---|---|---|
| Defoamer dispersion | 1 month clear oil phase [ml] % | 3 months |
| KS6 M | 0 | 0 |
| KS6 S | 0 | 0 |
| D10 M | 60 | 60 |
| D10 S | 27 | 50 |

Figure 1:
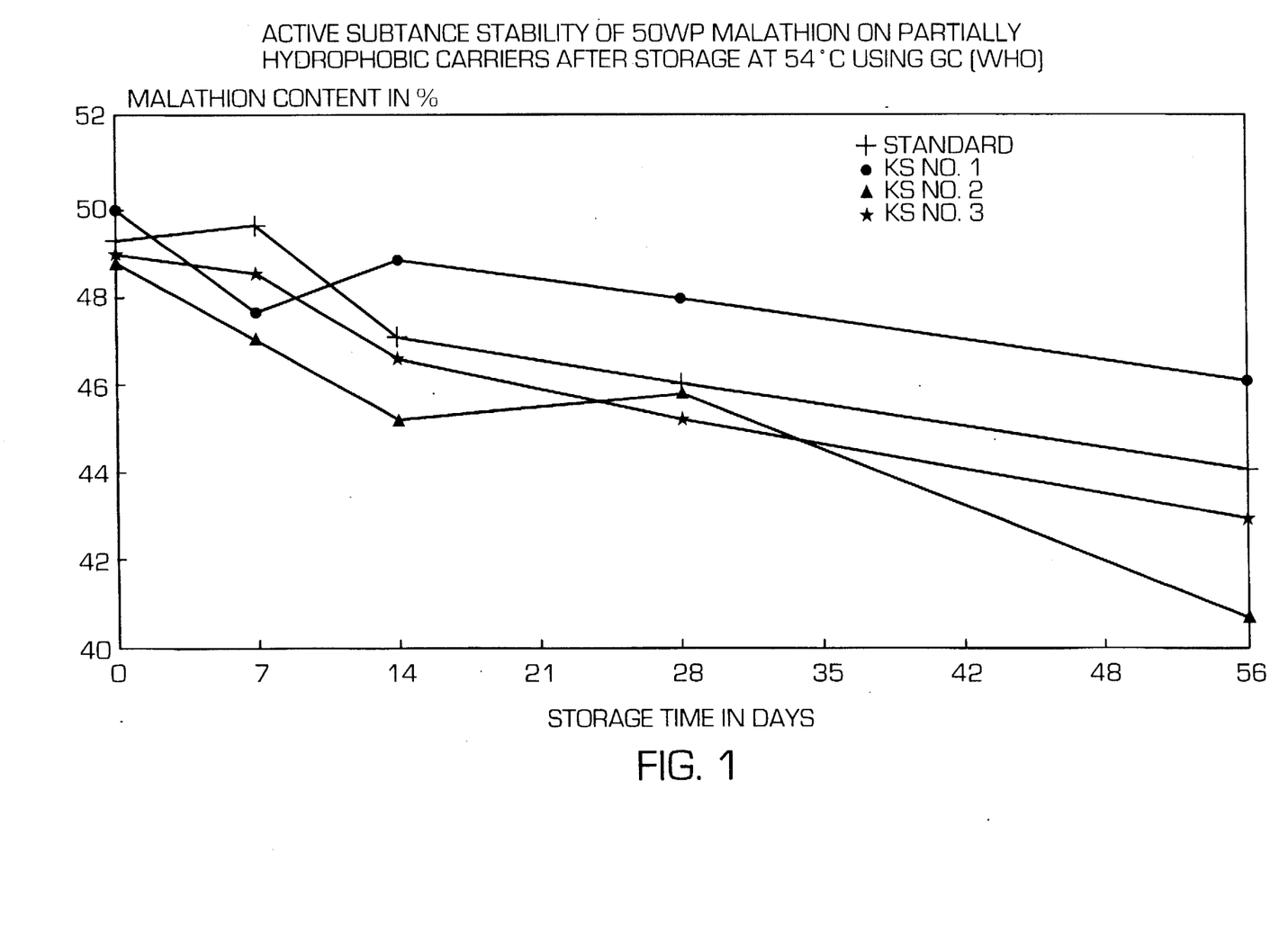
FIG. 1—Active substance stability of 50 WP malathion on partially hydrophobic carriers after storage at 54° C. using GC (WHO) is shown in graph of malathion content in percent versus storage time in days.
Figure 2:
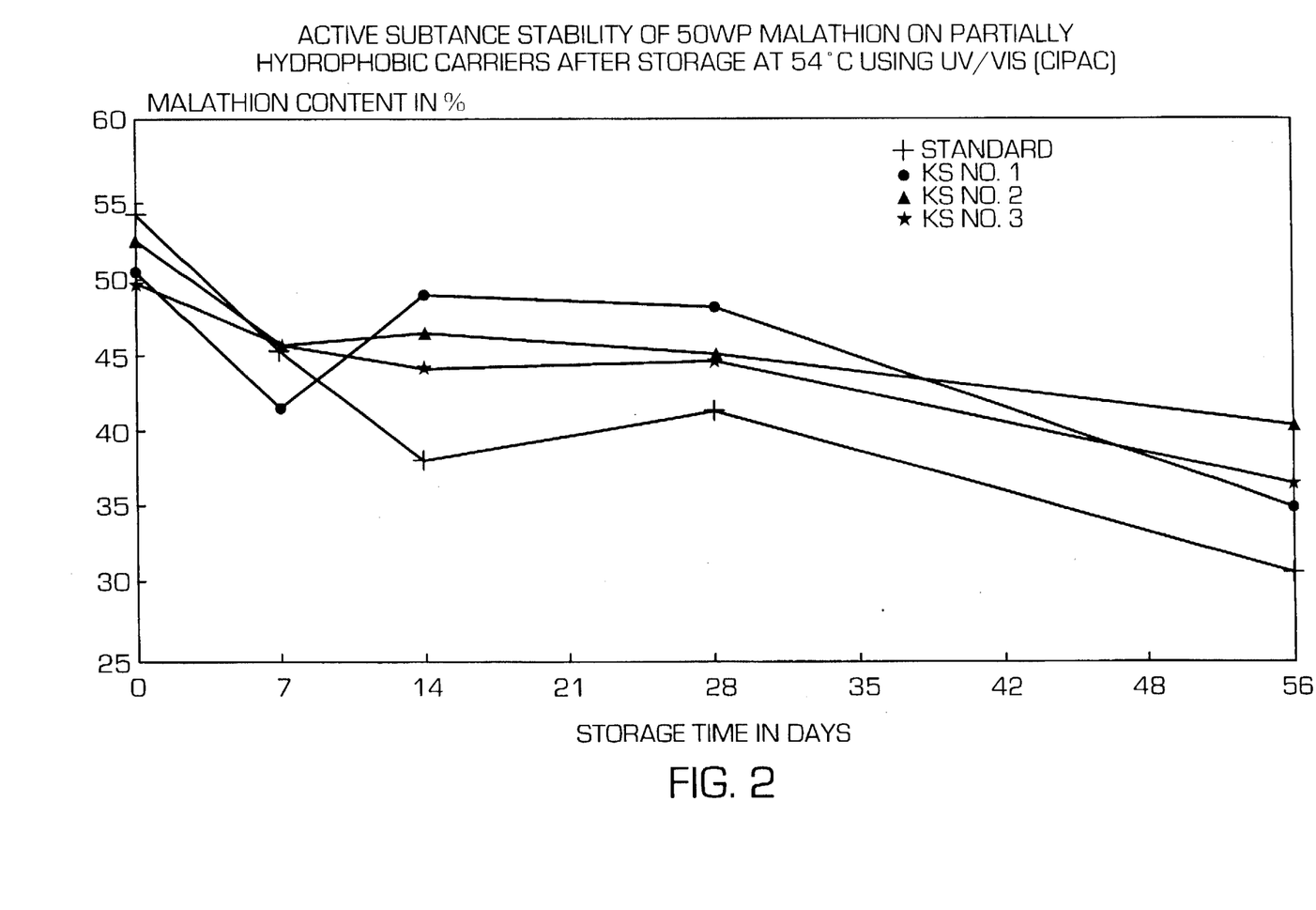
FIG. 2—Active substance stability of 50 WP malathion on partially hydrophobic carriers after storage at 54° C. using UV/VIS (CIPAC) is shown in graph of malathion content in percent versus storage time in days.
Figure 3:
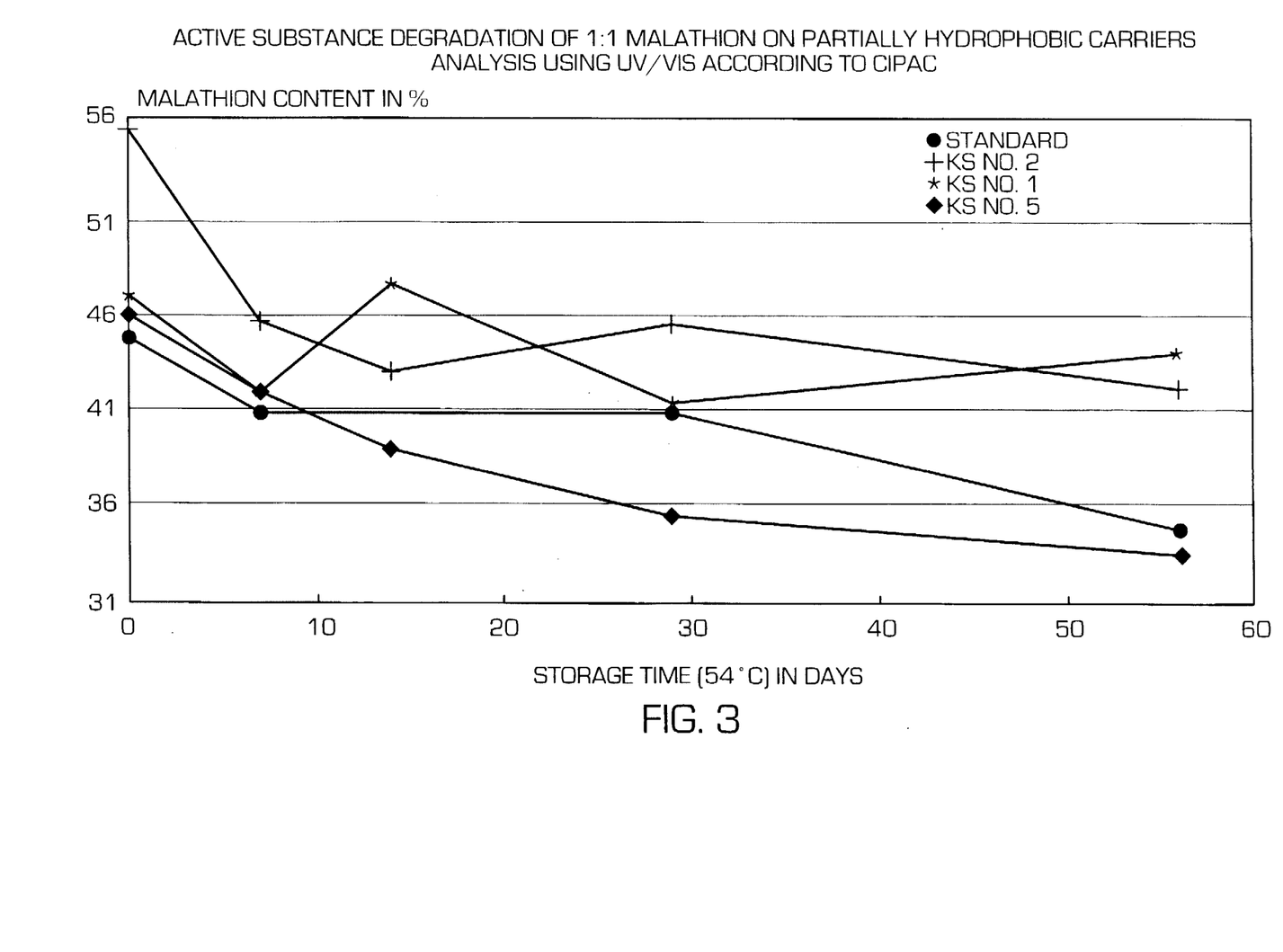
FIG. 3—Active substance degradation of 1:1 malathion on partially hydrophobic carriers, analysis using UV/VIS according to CIPAC is shown in graph of malathion content in percent versus storage time in days.
Figure 4:
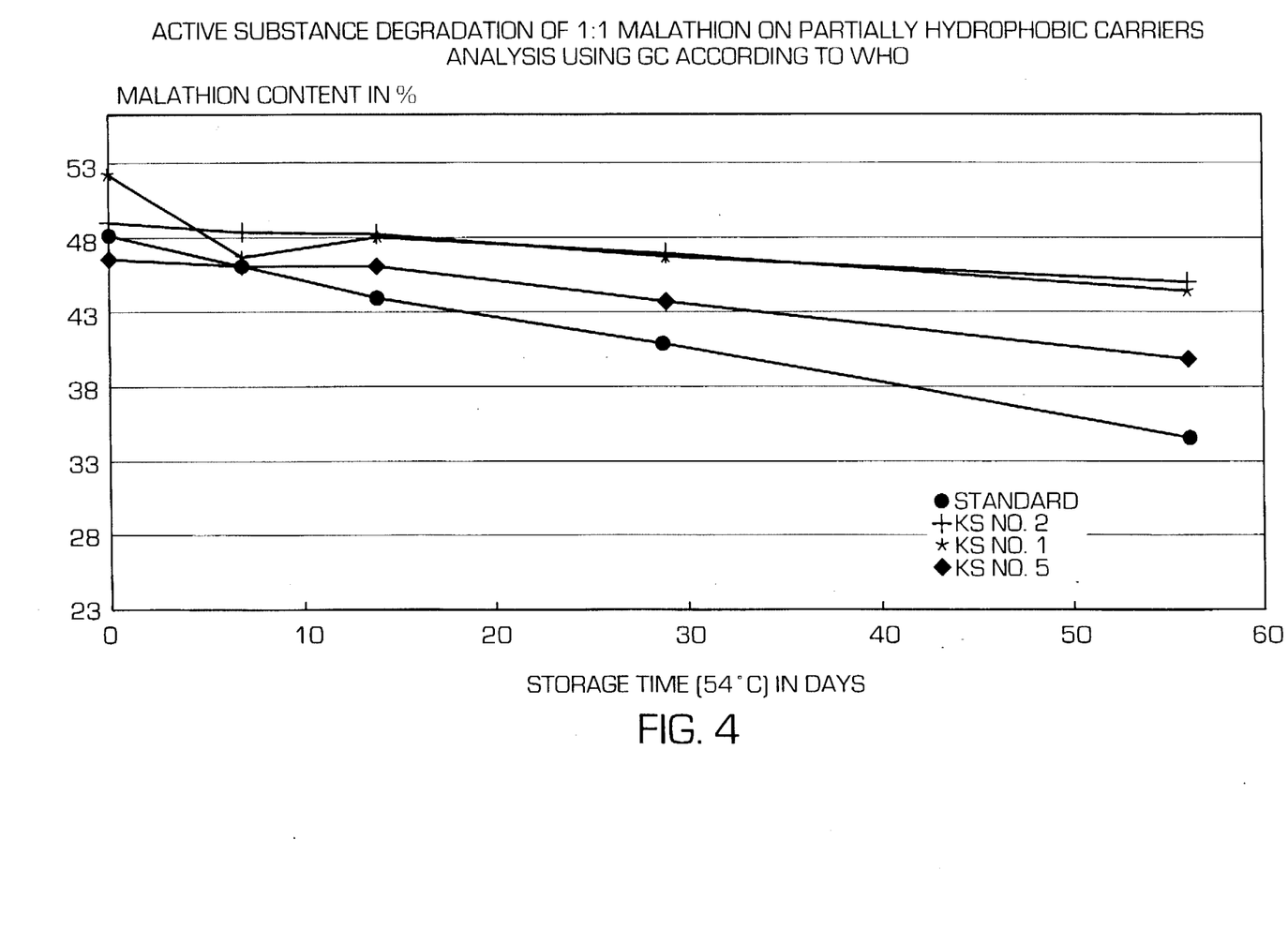
FIG. 4—Active substance degradation of 1:1 malathion on partially hydrophobic carriers, analysis using GC according to WHO is shown in graph of malathion content in percent versus storage time in days.
Figure 5:
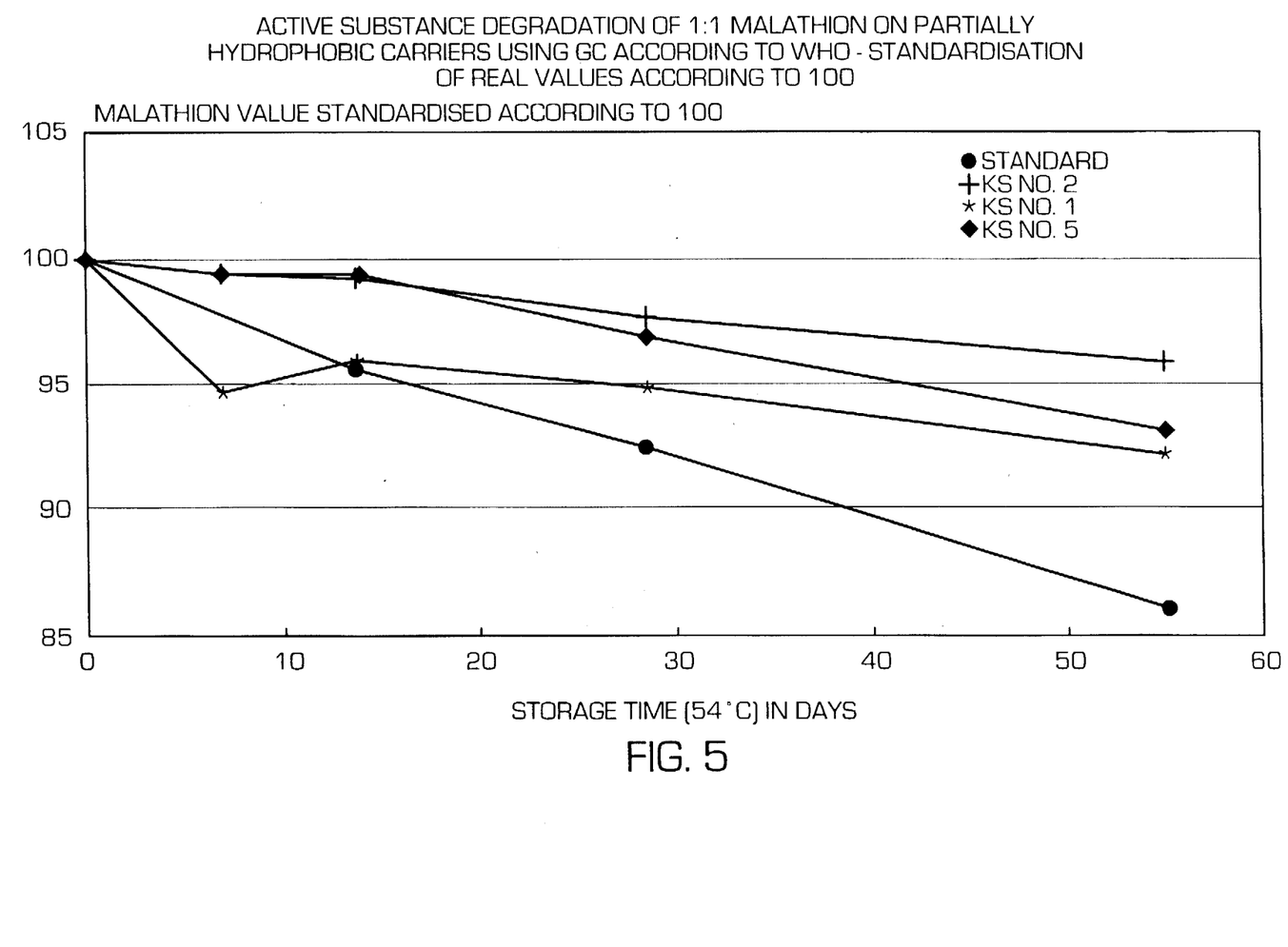
FIG. 5—Active substance degradation of 1:1 malathion on partially hydrophobic carriers using GC according to WHO with the standardization of real values according to 100 is shown in graph of malathion content in percent versus storage time in days.
Figure 6:
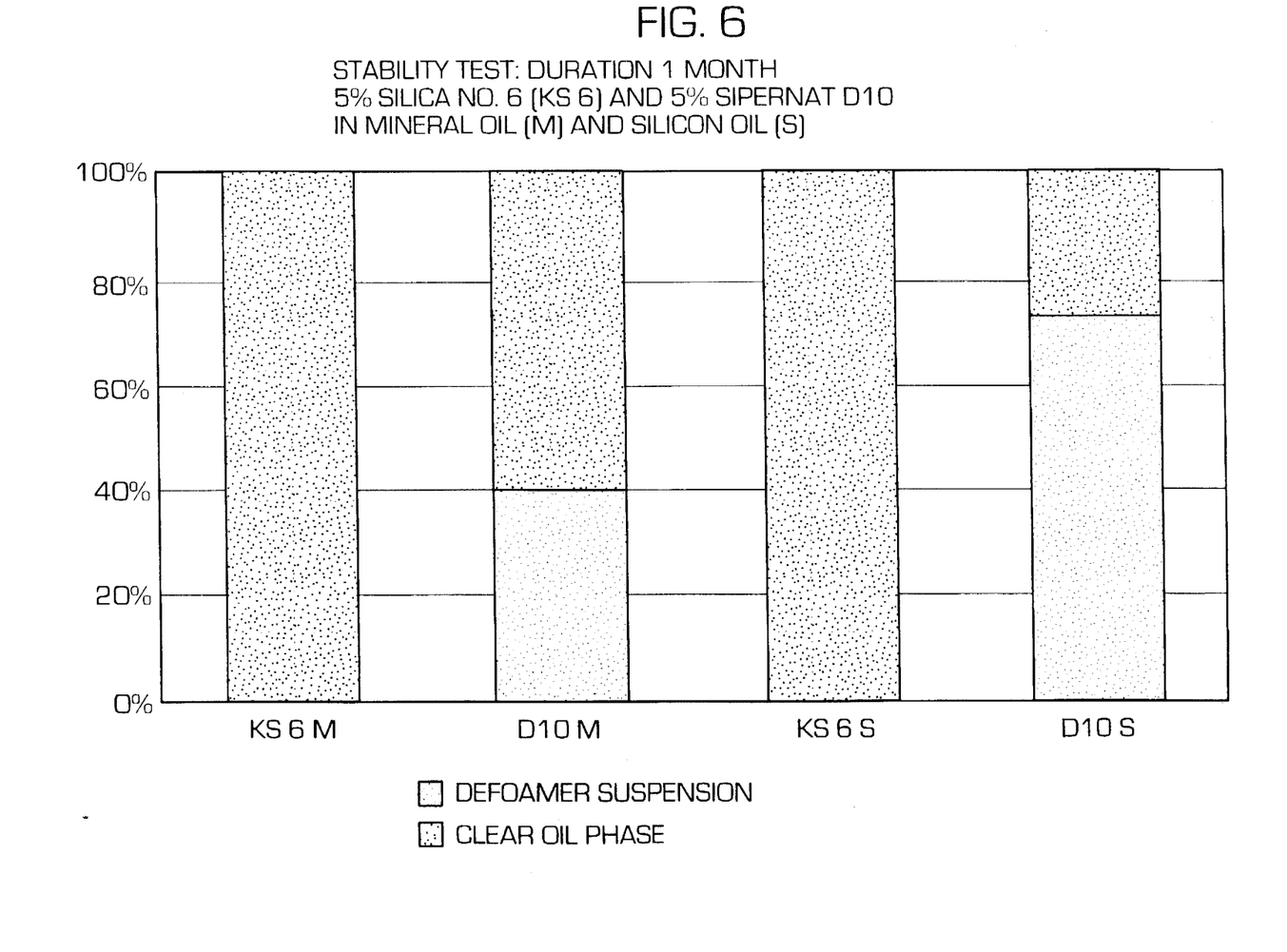
FIG. 6—Results of a stability test is shown of the defoamer suspension and the clear oil phase for precipitated silica of the invention (5% by weight in mineral oil and silicone oil) and Sipernat D10 (5% by weight in mineral oil and silicone oil) for a duration of one month.
Figure 7:
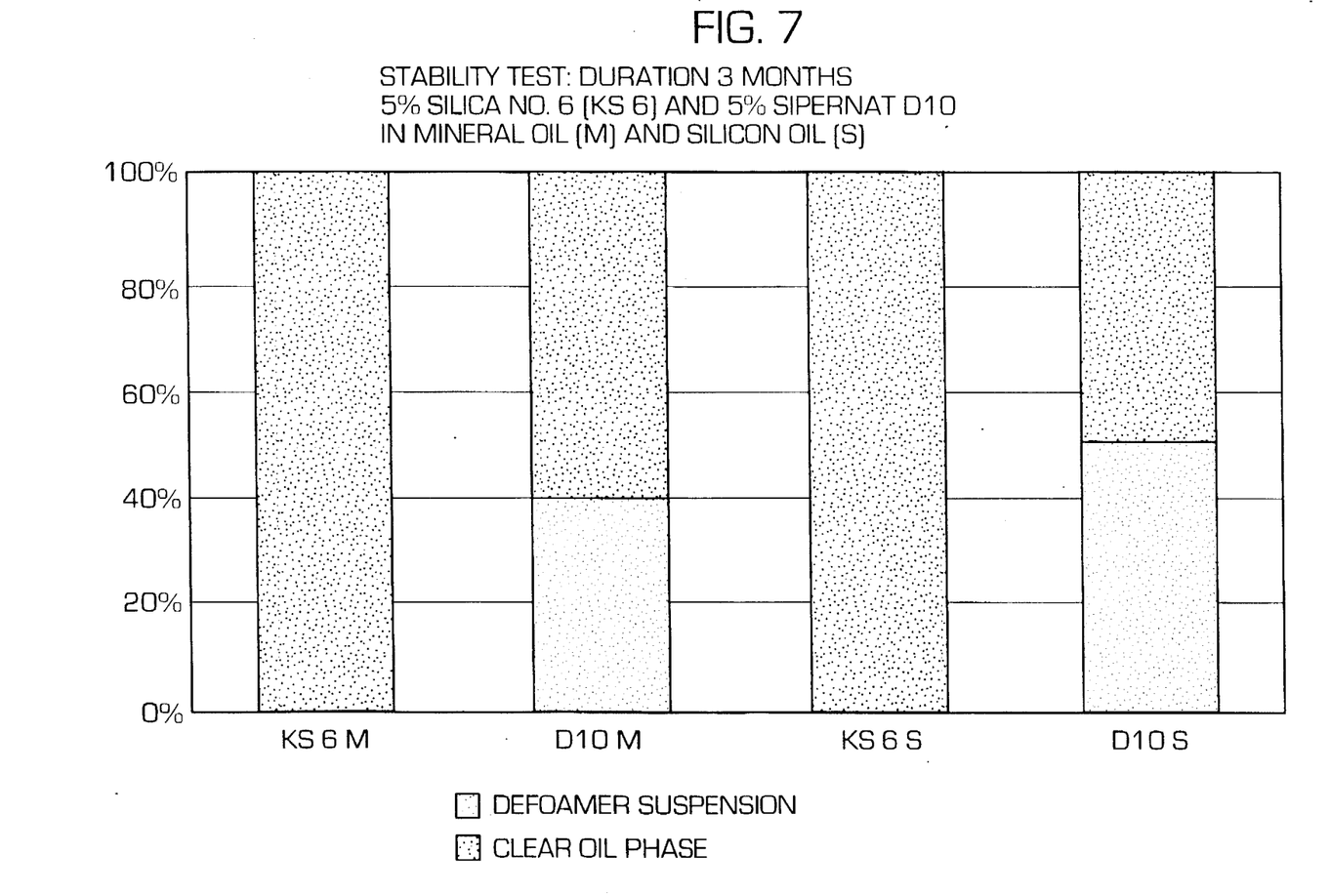
FIG. 7—Results of stability test is shown of the defoamer suspension and the clear oil phase for precipitated silica of the invention (5% by weight in mineral oil and silicone oil) and Sipernat D10 (5% by weight in mineral oil and silicone oil) for a duration of three months.

KS6 M = silica No. 6 in mineral oil
KS6 S = silica No. 6 in silicone oil
D10 M = Sipernat D10 in mineral oil
D10 S = Sipernat D10 in silicone oil FIGS. 6 and 7

FIGS. 6 and 7 show that the precipitated silica of the invention, worked into mineral oil and silicone oil, shows no phase separation at all after 3 months. A considerable phase separation is already encountered with the known Sipernat D10 both used oils after just one month.

Defoaming Testing Using Latex 160 g latex are weighed into a stainless steel beaker and foamed up for 3 minutes using a Hamilton-Beach-Scovill mixer in switch setting L (lowest stirrer speed: approximately 4000 rpm) after adding 0.3 g defoaming agent. The weight of 100 ml of this foam is determined by differential weighing in a stainless steel measuring cylinder. A high latex weight (almost 100 g) indicates a good defoaming capacity of the corresponding sample. The mean values are determined from at least two single determinations. A Hamilton-Beach-Scovill mixer is a milkshake mixer normally put to household use which can be set at three stirrer speeds (L, M and H). The switch setting "L" means approximately 4000 rpm. The substance to be stirred up is stirred up using a paddle stirrer with moveable "paddles."

$$\frac{100 \text{ g-weighed latex weight g after adding defoaming agent}^{*1}}{100 \text{ g-weighed blank value}^{*2} \text{ [g]}} \times 100$$

*1: differential weighing after adding the corresponding defoaming agent for latex dispersion and subsequent stirring for three minutes

*2: differential weighing after stirring the latex dispersion for three minutes without adding defoaming agent Formula for Calculating Foam Content in % After Performing the Latex Test $$\frac{100 \text{ g-weighed latex weight g after adding defoaming agent}^{*1}}{100 \text{ g-weighed blank value}^{*2} \text{ [g]}} \times 100$$

*1: differential weighing after adding the corresponding defoaming agent for latex dispersion and subsequent stirring for three minutes

*2: differential weighing after stirring the latex dispersion for three minutes without adding defoaming agent

Figure 8:
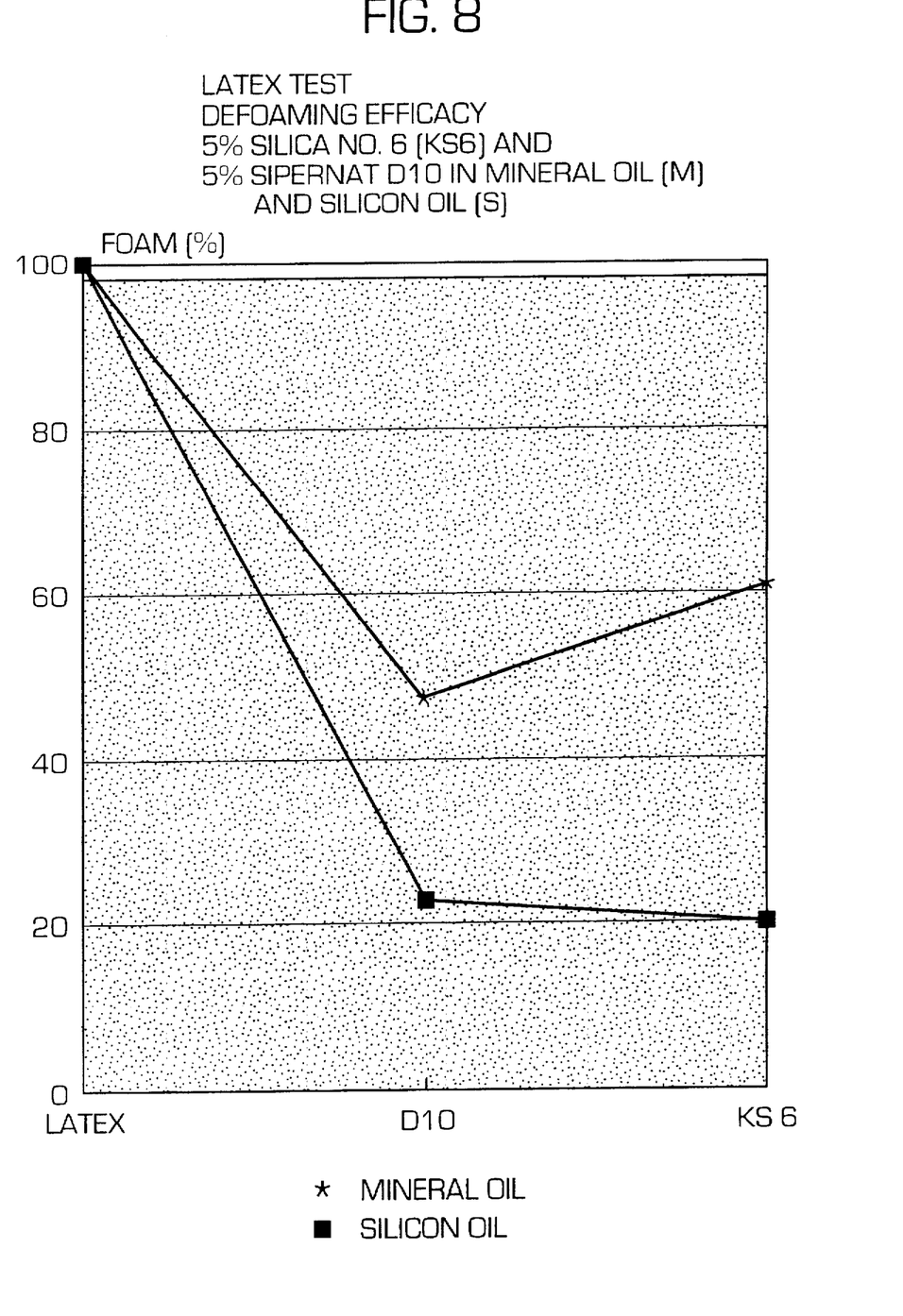
FIG. 8—Results of a latex test is shown of the defoaming effect of precipitated silica of the invention (5% in mineral oil and silicone oil) and Sipernat D10 (5% in mineral oil and silicone oil).

FIG. 8

FIG. 8 shows that while the precipitated silica of the invention displays a marginally lower defoaming effect than Sipernat D10 in mineral oil, this result must not necessarily continue in subsequent technical application tests, but that the stability is far better than with Sipernat D10. In silicone oil, the precipitated silica of the invention displays an identical defoaming effect to Sipernat D10.

The investigations conducted show that the stability of a defoaming dispersion can be substantially improved using the partially hydrophobic precipitated silica of the invention, whereas the defoaming effect is comparable with a known fully hydrophobic precipitated silica.

Further variations and modifications will be apparent to those skilled in the art from the foregoing and are intended to be encompassed by the claims appended hereto. German priority application 196 12 501.4 is relied on and incorporated herein by reference. The following "DIN's" are incorporated herein by reference:
DIN ISO 787/11
DIN ISO 787/2
DIN ISO 3262/11
DIN ISO 787/9
DIN ISO 3262/19
DIN 66131
DIN 55921
DIN 53200

We claim:

1. A partially hydrophobic precipitated silica, having the following properties:
    a methanol wettability of 10–49%,
    a mean particle size of 1 to 12 μm, and
    a carbon content of 0.3 to 1.85%.

2. The partially hydrophobic precipitated silica as defined in claim 1, wherein said silica has a DBP uptake as a dried substance of greater than 250 g/100 g.

3. The partially hydrophobic precipitated silica as defined in claim 1, wherein said silica has a loss on drying for two hours at 105° C. of 2.6 to 10%.

4. The partially hydrophobic precipitated silica as defined in claim 3, wherein said silica has a pH of 5.5 to 10 in a 5% methanol-aqueous solution.

5. The partially hydrophobic precipitated silica as defined in claim 1, with a pH value of 5.5 to 10 in a 5% methanol-aqueous solution.

6. A process for preparing the partially hydrophobic precipitated silica according to claim 1, comprising:
    mixing a water-repellent agent with a precipitated silica suspension using high shearing forces; and
    filtering said water-repellent agent-containing precipitated silica suspension to form a filter cake,
    wherein said partially hydrophobic precipitated silica has a methanol wettability of 10–49%.

7. The process according to claim 6, wherein said water-repellent agent-containing precipitated silica suspension is mixed in a predetermined ratio, at a pH of 3, and for a residence time in the mixer of no more than 5 seconds.

8. The process according to claim 7, further comprising:
    washing said filter cake to remove salt, and
    forming a filter cake having a homogenous mixture of precipitated silica and water-repellent agent.

9. The process according to claim 8, further comprising drying said homogenous filter cake.

10. The process according to claim 9, further comprising thermally post-treating or tempering said dried filter cake.

11. The process according to claim 9, further comprising milling said dried, treated filter cake to form said partially hydrophobic precipitated silica.

12. A composition, comprising the partially hydrophobic precipitated silica as defined in claim 1 and a hydrolysis-sensitive active substance, wherein said active substance is carried on said silica.

13. The composition as defined in claim 12, wherein said hydrolysis-sensitive active substance is a phosphoric acid ester.

14. The composition as defined in claim 12, wherein said composition is a crop protection agent.

15. A method of defoaming, comprising adding the partially hydrophobic precipitated silica as defined in claim 1 with a liquid composition to be defoamed.

16. A precipitated silica suspension comprising:
    85–98% by weight of said hydrophobic precipitated silica as defined in claim 1; and
    2–15% by weight of a water-repellent agent.

17. The precipitated silica suspension as defined in claim 16, wherein said water-repellent agent comprises silicone oil.

18. The precipitated silica suspension as defined in claim 17, wherein said silicone oil comprises dimethylpolysiloxanes having a viscosity of 20–100 mPas.

19. The precipitated silica suspension silica as defined in claim 17, wherein said dimethylpolysiloxanes have a viscosity of 50 mPas.

* * * * *